United States Patent [19]
Amariglio et al.

[11] Patent Number: 5,414,176

[45] Date of Patent: * May 9, 1995

[54] METHOD FOR CONVERTING METHANE INTO HIGHER HYDROCARBONS

[75] Inventors: Henri Amariglio, Nancy; Jacques J. Saint Just, Le Pecq, both of France

[73] Assignee: GAZ de France, Paris, France

[*] Notice: The portion of the term of this patent subsequent to Feb. 9, 2011 has been disclaimed.

[21] Appl. No.: 842,091

[22] Filed: Mar. 19, 1992

[30] Foreign Application Priority Data

Jul. 20, 1990 [FR] France .................... 90 09340

[51] Int. Cl.$^6$ ............................ C07C 2/10
[52] U.S. Cl. ........................ 585/500; 585/700; 585/943
[58] Field of Search ............... 585/943, 500, 700

[56] References Cited

U.S. PATENT DOCUMENTS

| | | | |
|---|---|---|---|
| 1,698,602 | 1/1929 | Mittasch et al. | 585/943 |
| 2,537,688 | 1/1951 | Mosesman | 585/943 |
| 4,009,219 | 2/1977 | Tamers | 423/439 |
| 4,801,762 | 1/1989 | Leyshon | 585/905 |
| 4,879,427 | 11/1989 | Sofranko | 585/500 |
| 4,962,261 | 10/1990 | Abrevaya et al. | 585/500 |
| 5,132,481 | 7/1992 | Do et al. | |

FOREIGN PATENT DOCUMENTS 2213828  8/1989  United Kingdom.

*Primary Examiner*—Anthony McFarlane
*Attorney, Agent, or Firm*—Ostrolenk, Faber, Gerb & Soffen

[57] ABSTRACT

The invention relates to a method for converting methane into higher hydrocarbons. According to the invention, a catalyst comprised essentially of a metal belonging to the series of transition metals and of a carrier which is comprised particularly of a refractory metal oxide is subjected to a methane flow at a temperature comprised between 100° C. and 300° C. approximately, with a contact time of at least one second, and to a hydrogen flow at a temperature comprised between 100° C. and 300° C. with a contact time of at least one second. The method of the invention is particularly usable in chemical engineering.

10 Claims, No Drawings

METHOD FOR CONVERTING METHANE INTO HIGHER HYDROCARBONS

BACKGROUND OF THE INVENTION

1. Field of the Invention

The present invention has as its subject a method of conversion of methane into higher hydrocarbons and more especially into $C_2$ to $C_7$ hydrocarbons.

2. Description of the Related Art

The conversion of methane into higher hydrocarbons and hydrogen is disadvantaged thermodynamically. Conventionally, the main route of conversion of methane is the endothermic reaction of manufacturing synthesis gas by steam reforming. This route has limits bound to thermodynamics and to implementing which have led to the search for alternatives. In the search for favorable thermodynamic reactions, one solution has been studied recently, the oxidizing coupling, which consists in catalytically reacting the methane in the presence of oxygen for converting it into a mixture of ethane and ethylene. However this solution has proved to be unsatisfactory because it does not lead to a sufficiently selective process for the production of higher hydrocarbons. In effect in addition to the unavoidable formation of water, it leads to a substantial formation of undesirable secondary products and notably to that of carbon oxides.

SUMMARY OF THE INVENTION

The present invention is based upon the unexpected discovery that one may obtain a methane conversion without any gaseous co-reagent with a maximum selectivity and without any substantial loss of material upon passing round the thermal dynamic and kinetic difficulties by an original cyclic process associated with a choice of adapted catalysts.

Therefore the present invention has as its subject a method of conversion of methane into higher hydrocarbons which consists in exposing a catalyst consisting essentially of a metal belonging to the series of transition metals and a support with a large specific surface which consists in particular of oxide of refractory metal to a methane flow, at a temperature comprised between 100° and 300° C. with a contact time of at least one second, then to a hydrogen flow at a temperature comprised between 100° and 300° C. with a contact time of at least one second.

According to a characteristic of the invention the catalyst is constituted of a metal selected in the group consisting of Pt, Ru, Pd, Ir, Rh, Re, Co, Ni, Fe, W and their mechanical mixtures and/or their alloys and their promoters of alkali or alkaline-earth metals and of a support with a large specific surface which is constituted of oxide of a refractory metal selected notably in the group consisting of silica, alumina, silica-alumina, zinc oxides, magnesium, chromium, zirconium and rare earths or active coal.

Still according to a characteristic of the invention the temperature is comprised between about 130° C. and 250° C.

According to still another characteristic, the contact time is comprised between 12 and 480 seconds.

Still according to a characteristic of the invention the method in addition consists in recovering the hydrogen flow by separating the hydrogen from the products obtained.

According to a peculiarity of the invention a complement of hydrogen may be obtained by catalytic reforming of the mixture of the obtained products.

According to another peculiarity of the invention the method consists in the successive and non interrupted performance of the previously described steps.

Other objects, details and advantages of the present invention will appear more clearly upon the reading of the detailed description which will follow.

DESCRIPTION OF THE PREFERRED EMBODIMENT

More particularly the elementary cycle of the method consists in successively exposing the catalyst to a flow of methane and then to hydrogen. The method consists in the successive continuous repetition of the elementary cycle. This may be carried out notably by passing a methane flow and a hydrogen flow onto the catalyst in an alternate manner or by circulating the catalyst successively in methane and then in hydrogen.

In the first case the catalyst may be in the form of a fixed bed in particular in a monolithic form but it is preferably fluidized to ensure an identical contact time between all catalyst particles and the methane as well as an uniform temperature.

In the second case the catalyst is in the form of a circulating fluidized bed.

When the conversion reaction proper is completed a gaseous flow consisting of hydrogen and of a mixture of light ($C_2$–$C_5$) alkanes is recovered. A separation is effected between the hydrogen intended to be recycled and the light alkanes which are the sought products. It is to be noted that although the complete conversion cycle globally is a hydrogen producer $nCH_4 \rightarrow C_nH_{2n+2} + (n-1)H_2$, it is in practice a consumer since the hydrogen is produced in a very dilute way and therefore is non recoverable in the flow of methane during the first step of the method which corresponds to the adsorption and to the condensation of the adsorbed methane. The second step, i.e. the sweeping with hydrogen is hydrogen consuming. The upper limit of hydrogen consumption may be evaluated by considering that all the alcanes which are then produced are adsorbed in the form of olefines. The hydrogen consumption is the amount necessary for converting the olefines into alkanes. One is thus led to about 70 tons of hydrogen consumed per ton of $C_2$–$C_5$ product, hence a quantity comparable with those which are encountered in the hydrotreatment of petroleum cuts. The hydrogen consumption plays an important role in the competitivity of the methods.

The output depends upon the frequency at which the cyclic process can be repeated. The as short as possible contact times are therefore sought for, such as contact times of 12 to 480 seconds or less. The most active catalysts permit to reduce the contact time necessary for the adsorption, for the conversion of methane and for the desorption of the products obtained. After the desorption the catalyst is thus regenerated and the cyclic process ready to be worked again.

As one will make it evident hereinafter the nature of the metal(s), support(s), promoter(s) and the state of dispersion of the metal on the support are conditioning the activity of the catalyst and therefore the contact times.

A number of tests have been carried out with different types of catalysts. The results of these tests are reported in the table hereinafter.

| Kind of catalyst | 5% Ru/activated carbon | 10% Ru/SiO$_2$ | 5% Ru/Al'$_2$O$_3$ | Co/Kieseiguhr | 5% Pt/activated carbon | 5% Pt/SiO$_2$ | 5% Pt/SiO$_2$ |
|---|---|---|---|---|---|---|---|
| Mass of catalyst (g) | 0.6 | 0.5 | 0.6 | 0.6 | 0.6 | 0.1 | 0.1 |
| Temperature °C. | 200 | 130 | 150 | 250 | 275 | 250 | 250 |
| Exposition Time with CH$_4$ (s) | 480 | 300 | 480 | 480 | 480 | 300 | 30 |
| Exposition Time with H$_2$ (s) | 12 | 12 | 12 | 12 | 12 | 12 | 10 |
| Debit CH$_4$, (l/h) | 15.0 | 6.0 | 15.0 | 18.0 | 12.0 | 24.0 | 24.0 |
| Debit H$_2$, (l/h) | 7.2 | 7.2 | 7.2 | 7.2 | 7.2 | 7.2 | 7.2 |
| Amount of converted CH$_4$/g cata g | $1.28 \cdot 10^{-3}$ | $0.11 \cdot 10^{-3}$ | $1.34 \cdot 10^{-3}$ | $0.58 \cdot 10^{-3}$ | $0.95 \cdot 10^{-3}$ | $0.24 \cdot 10^{-3}$ | $2.4 \cdot 10^{-3}$ |
| Conversion, % (converted CH$_4$/ CH$_4$ entering) | 0.10 | 0.03 | 0.11 | 0.04 | 0.08 | 0.16 | 1.7 |

As it appears from the table hereinabove, the best conversions and therefore the best outputs—since the selectivity for the mixture of higher alkanes is 100%—are obtained with a platinium—based catalyst onto a silica support.

It is to be noted that one may adapt the present method to the production of heavier (up to C$_7$) hydrocarbons by increasing the time of contact with the catalyst.

The invention is of course not limited to the examples given hereinabove.

We claim:

1. Method for converting methane into higher hydrocarbons, consisting essentially of the steps of exposing a catalyst comprising a transition metal and a support comprising a refractory metal oxide having a large specific surface, to a flow of a gas consisting essentially of methane at a temperature between about 100° and 300° C. for a contact time of at least one second, then exposing said catalyst to a hydrogen flow at a temperature between 100° and 300° C. for a contact time of at least one second, recovering a gaseous effluent consisting of said higher hydrocarbons and hydrogen, and separating the higher hydrocarbons from the hydrogen.

2. Method according to claim 1, wherein the metal is selected from the group consisting at Pt, Ru, Ir, Rh, Re, Co, Ni, Fe, W, and mixtures thereof.

3. Method according to claim 1, wherein the support is a refractory metal oxide selected from the group consisting of silica, alumina, silica-alumina, zinc oxide, magnesium oxide, chromium oxide, zirconium oxide, rare earth oxide and active coal.

4. Method according to claim 1, wherein the temperature for exposure to the methane flow and the hydrogen flow is between 130° C. and 250° C.

5. Method according to claim 1, wherein the contact time for exposure to both the methane flow and the hydrogen flow is between 12 seconds and 480 seconds.

6. Method according to claim 1, wherein the method is continuous.

7. Method according to claim 1, wherein said catalyst further comprises a promoter.

8. Method according to claim 7, wherein said promoter is selected from the group consisting of alkali and alkaline-earth metals.

9. Method according to claim 1, wherein said higher hydrocarbons consist of C$_2$-C$_5$ alkanes.

10. Method for converting methane into higher hydrocarbons, consisting essentially of the steps of exposing a catalyst comprising a transition metal and a support comprising a refractory metal oxide having a large specific surface to a flow of gas consisting essentially of methane at a temperature between about 100° C. and 300° C. for a contact time of at least one second, then exposing said catalyst to a hydrogen flow at a temperature between 100° C. and 300° C. for a contact time of at least one second, recovering a gaseous effluent consisting of said higher hydrocarbons and hydrogen, separating the higher hydrocarbons from the hydrogen, and recycling said hydrogen to the step of exposing the catalyst to said hydrogen flow.

* * * * *